(12) United States Patent
Meng et al.

(10) Patent No.: US 11,045,644 B2
(45) Date of Patent: Jun. 29, 2021

(54) CUFF ELECTRODE WITH LYSING AGENT

(71) Applicants: UNIVERSITY OF SOUTHERN CALIFORNIA, Los Angeles, CA (US); HUNTINGTON MEDICAL RESEARCH INSTITUTES, Pasadena, CA (US)

(72) Inventors: Ellis Meng, Los Angeles, CA (US); Victor Pikov, Los Angeles, CA (US)

(73) Assignees: UNIVERSITY OF SOUTHERN CALIFORNIA, Los Angeles, CA (US); HUNTINGTON MEDICAL RESEARCH INSTITUTES, Pasadena, CA (US)

( * ) Notice: Subject to any disclaimer, the term of this patent is extended or adjusted under 35 U.S.C. 154(b) by 501 days.

(21) Appl. No.: 15/752,110

(22) PCT Filed: Aug. 12, 2016

(86) PCT No.: PCT/US2016/046802
§ 371 (c)(1),
(2) Date: Feb. 12, 2018

(87) PCT Pub. No.: WO2017/078819
PCT Pub. Date: May 11, 2017

(65) Prior Publication Data
US 2020/0206496 A1    Jul. 2, 2020

Related U.S. Application Data

(60) Provisional application No. 62/204,862, filed on Aug. 13, 2015.

(51) Int. Cl.
| | | |
|---|---|---|
| A61N 1/05 | (2006.01) | |
| A61B 5/00 | (2006.01) | |
| A61B 5/24 | (2021.01) | |

(52) U.S. Cl.
CPC .............. *A61N 1/0556* (2013.01); *A61B 5/24* (2021.01); *A61B 5/6877* (2013.01); *A61B 2562/125* (2013.01)

(58) Field of Classification Search
CPC ........... A61L 31/10; A61N 1/05; H01R 43/00; A61B 5/04
(Continued)

(56) References Cited

U.S. PATENT DOCUMENTS

| | | | |
|---|---|---|---|
| 4,602,624 | A | 7/1986 | Naples et al. |
| 5,824,027 | A | 10/1998 | Hoffer et al. |

(Continued)

FOREIGN PATENT DOCUMENTS

| | | |
|---|---|---|
| DE | 10 2007 036862 A1 | 2/2009 |
| WO | 2006 098996 A1 | 9/2006 |

OTHER PUBLICATIONS

International Search Report and Written Opinion issued in Application No. PCT/US2016/046802, dated Jun. 6, 2017.

*Primary Examiner* — Jon Eric C Morales
(74) *Attorney, Agent, or Firm* — Michael Best & Friedrich LLP (57) ABSTRACT

A new class of peripheral nerve interfaces that combines microfluidics with microelectronics. A peripheral nerve interface that allows intraneural targeting through the combined use and sequential application of lysing agents and neurotrophic factors.

27 Claims, 12 Drawing Sheets

(58) Field of Classification Search
USPC .................................................. 600/373, 377
See application file for complete search history.

(56) References Cited

U.S. PATENT DOCUMENTS

| | | |
|---|---|---|
| 6,308,105 B1 | 10/2001 | Duysens et al. |
| 2008/0319506 A1 | 12/2008 | Cauller |
| 2009/0293270 A1 | 12/2009 | Brindley et al. |
| 2010/0121422 A1 | 5/2010 | Jolly et al. |
| 2011/0021943 A1 | 1/2011 | Lacour et al. |
| 2011/0251473 A1* | 10/2011 | Moran ................. A61N 1/0551 600/373 |
| 2012/0323102 A1* | 12/2012 | Tang .................... A61N 1/0558 600/377 |
| 2014/0228738 A1 | 8/2014 | Park et al. |
| 2015/0202351 A1* | 7/2015 | Kaplan ................ A61B 5/6868 607/116 |
| 2015/0224326 A1 | 8/2015 | Toth et al. |

* cited by examiner

CUFF ELECTRODE WITH LYSING AGENT

CROSS-REFERENCE TO RELATED APPLICATION(S)

This is a U.S. national stage entry of International Patent Application No. PCT/US2016/046802, filed on Aug. 12, 2016, which claims priority to U.S. Provisional Patent Application No. 62/204,862, filed on Aug. 13, 2015, the entire contents of each of which are fully incorporated herein by reference.

STATEMENT REGARDING FEDERALLY SPONSORED RESEARCH OR DEVELOPMENT

This invention was made with government support under HR0011-15-2-0006 awarded by the Defense Advanced Research Projects Agency. The government has certain rights in the invention.

BACKGROUND OF THE INVENTION

Electrical interfaces to the peripheral nerves are either extraneural or intrafascicular/intraneural. Extraneural electrodes, such as cuff electrodes, are placed on the circumference of the nerve. Given their exterior location relative to epineurium, these electrodes are largely isolated from the activity in individual axonal fibers. Better access to individual fascicles has been achieved by reshaping peripheral nerves by flattening (as in the flat interface nerve electrode, FINE) however, their signal-to-noise ratio is still restricted by the epineurium and the reshaping process can induce nerve damage.

Intrafascicular/intraneural electrodes gain greater access to the central axon population and can selectively target smaller groups of axons but at the cost of greater invasiveness. Electrodes may either be inserted longitudinally into the nerve and run parallel to nerve fibers or transversely and run perpendicular to fibers. Of the two methods, transverse electrodes are associated with greater risk of nerve damage. Invasively inserted electrodes are fabricated from materials with high elastic modulus several orders of magnitude greater than that of nerve, contributing to chronic tissue response and the lack of recording/stimulation stability over time. Although another class of regenerative electrodes in the form of sieve or tubular structures exist, they are not considered in the context of electrodes that can be applied to intact nerves.

SUMMARY OF THE INVENTION

Currently, there are no methods to achieve fascicular selectivity with non-invasive cuff electrodes. Regardless of placement of the electrode with respect to the nerve (extraneural, intrafascicular, intraneural), stability of the interface for chronic robust recordings remains a challenge. To overcome these technical hurdles, embodiments of the present invention involve a new non-invasive approach that obtains access to fascicles by first locally disrupting the epineurium and perineurium (these protective sheaths are primarily composed of collagen) with a collagen-lysing agent. Once the collagen is transiently disrupted, collateral axonal sprouting towards the microchannels and associated electrodes on the cuff may be achieved using neurotrophic factors. The purpose of this multi-step approach is to establish a chronically stable peripheral nerve interface capable of high signal-to-noise ratio recordings. This approach intentionally maintains the non-invasiveness of the extraneural cuff without requiring reshaping of the nerves by flattening.

This strategy to achieve fascicular selectivity with non-invasive cuff electrodes is provided in the Lyse-and-Attract Cuff Electrode (LACE) according to embodiments of the invention, which aims to target individual fascicles within a nerve using focused delivery of agents in conjunction with either traditional recording and stimulating electrodes or with chemically-induced stimulation or blockade of axonal conduction. The microchannels are used for long-term delivery of lysing agents and neurotrophic factors in order to attract the sprouting of axonal collaterals into the microchannel lumen, and the embedded recording/stimulation electrode sites are located inside the microchannel on its outer surface immediately opposite the outlet. Additional electrode sites may be located inside the microchannel distal to the outlet as well as on the surface of the cuff facing the nerve. The cuff includes an integrated ribbon cable that routes the electrical and fluidic connections to custom interconnects.

The Lyse-and-Attract Cuff Electrode (LACE) concept introduces a new class of peripheral nerve interfaces that combines, for the first time, microfluidics with microelectronics. Embodiments of the invention relate to a peripheral nerve interface that allows intraneural targeting via recording/stimulation electrodes through the combined use and sequential application of lysing agents and neurotrophic factors. This approach is better than the state of the art in that it achieves stability and fascicle specificity without physically damaging or penetrating the nerve. The proposed induction of collateral sprouting is based on a natural capacity of intact axons that was established 20 years ago (Viterbo, F., J. C. Trindade, K. Hoshino, and A. Mazzoni, *Two end-to-side neurorrhaphies and nerve graft with removal of the epineural sheath: experimental study in rats.* Br J Plast Surg, 1994. 47(2): p. 75-80.), and since then has been applied in surgical nerve repair using a technique of the end-to-side anastomosis (Tos, P., G. Colzani, D. Ciclamini, P. Titolo, P. Pugliese, and S. Artiaco, *Clinical Applications of End-to-Side Neurorrhaphy: An Update.* Biomed Res Int, 2014. 2014: p. 646128.). Both sensory and motor fibers appear to have equal capacity for collateral sprouting (Samal, F., P. Haninec, O. Raska, and P. Dubovy, *Quantitative assessment of the ability of collateral sprouting of the motor and primary sensory neurons after the end-to-side neurorrhaphy of the rat musculocutaneous nerve with the ulnar nerve.* Ann Anat, 2006. 188(4): p. 337-44.). Application of neurotrophic factors, such as NGF and methylcobalamin, can significantly enhance collateral sprouting from an intact nerve (McCallister, W. V., P. Tang, J. Smith, and T. E. Trumble, *Axonal regeneration stimulated by the combination of nerve growth factor and ciliary neurotrophic factor in an end-to-side model.* J Hand Surg Am, 2001. 26(3): p. 478-88; Liao, W. C., Y. J. Wang, M. C. Huang, and G. F. Tseng, *Methylcobalamin facilitates collateral sprouting of donor axons and innervation of recipient muscle in end-to-side neurorrhaphy in rats.* PLoS One, 2013. 8(9): p. e76302.). The sprouting can be further enhanced by microsurgical removal of epineurial and perineurial layers from the nerve (Liu, H. F., Z. G. Chen, T. L. Fang, P. Arnold, W. C. Lineaweaver, and J. Zhang, *Changes of the donor nerve in end-to-side neurorrhaphies with epineurial window and partial neurectomy: a long-term evaluation in the rat model.* Microsurgery, 2014. 34(2): p. 136-44; Haninec, P., R. Kaiser, and P. Dubovy, *A comparison of collateral sprouting of sensory and motor axons after end-to-side neurorrhaphy with and without the perineurial window.* Plast Reconstr Surg, 2012. 130(3): p. 609-14.). In contrast to the microsurgical removal of epineurium and perineurium, an enzymatic removal of collagen fibers was selected to avoid the risk of a nerve injury (Rydevik, B., M. D. Brown, T. Ehira, and C. Nordborg, *Effects of collagenase on nerve tissue. An experimental study on acute and long-term effects in rabbits*. Spine (Phila Pa. 1976), 1985. 10(6): p. 562-6.).

First, the collagen fibers of the epineurium and perineurium are transiently digested by localized intra-neural diffusion or infusion of collagenase, elastase, gelatinase, galactosidase, lactamase, glucuronidase, tripsin, fibrinolysin, papain, or another enzyme involved in digestion of the collagen-mucopolysaccharide-containing extracellular matrix from the closest microchannel outlet, thus removing any mechanical impediments to collateral sprouting. Then collateral sprouting may be selectively and atraumatically induced by localized diffusion or infusion of neurotrophic factors, such as NGF, BDNF, NT-3, NT-4, and methylcobalamin (for inducing, promoting, and spatially guiding the axonal sprouting toward the microchannel and associated electrode). Induction of collateral sprouting has never before been attempted in a cuff nerve device and can lead to a completely new type of a fascicle-specific, flexible, and reliable neural interface.

In one embodiment, the invention provides a cuff electrode comprising a substrate including an array of microchannels, at least one of the microchannels includes an inlet and an outlet, an electrode positioned adjacent to the outlet of the at least one microchannel, and a supply channel in fluid communication with the at least one microchannel, the supply channel providing a lysing agent or a neurotrophic factor to the outlet of the at least one microchannel.

In another embodiment, the invention provides a cuff electrode comprising a substrate including an array of microchannels, each of the microchannels having an inlet connected to a main supply channel, and an outlet positioned adjacent to a nerve, an electrode positioned in the microchannel for detecting or stimulating electrical activity of the nerve, an adjustable locking mechanism configured to position the substrate around a nerve having a diameter between about 1 mm and about 2 mm.

In other constructions, the electrode may be positioned adjacent to or at a distance from the first outlet.

In other constructions, embodiments of the invention can include a plurality of electrodes positioned at the first outlet, adjacent to the first outlet, or at a distance from the first outlet.

In other constructions, the invention can include a plurality of electrodes positioned on the surface of the cuff intended to face the nerve including on the exterior of any portion of the microchannel.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Electrical interfaces to peripheral nerves involve the placement of electrodes in close proximity to the nerves. While interfaces can be used for either electrophysiological recordings from nerves or stimulation of nerves, recording is more difficult and in practice, poses many technical challenges. This renders current peripheral nerve interface technologies inadequate for chronic clinical use.

Current approaches involve utilizing cuff electrodes placed on the circumference of the nerve or penetrating electrodes to bypass the insulating epineurium. Electrodes placed externally cannot access individual axonal fibers and hence result in recordings with low signal to noise ratio, poor spatial resolution, and poor fascicular selectivity. Invasive, penetrating approaches improve the spatial resolution and sensitivity of recordings at the risk of nerve damage.

To achieve the improved performance of penetrating electrode interfaces without having to damage the nerve, a cuff-style interface having both electrodes and microchannels is disclosed. The microchannels serve as conduits for delivery of chemicals such as lysing agents to digest the collagen fibers of the epineurium and perineurium to provide direct access to nerves. To further improve the proximity of the interface, the microchannels can also act as conduits to direct the delivery of neurotrophic factors that induce, promote, and spatially guide the sprouting of axons toward the microchannel and integrated electrode recording sites. The Lyse-and-Attract Cuff Electrode (LACE) approach disclosed herein overcomes the signal-to-noise limitations of the cuff-style nerve interfaces by attracting the sprouting of axonal collaterals while benefiting from the long term stability and non-invasiveness of the cuff form factor. Parylene micromachining technology is being applied to fabricate cuffs having a small form factor and allow interfaces with small diameter nerves (~1-2 mm).

Figure 1:
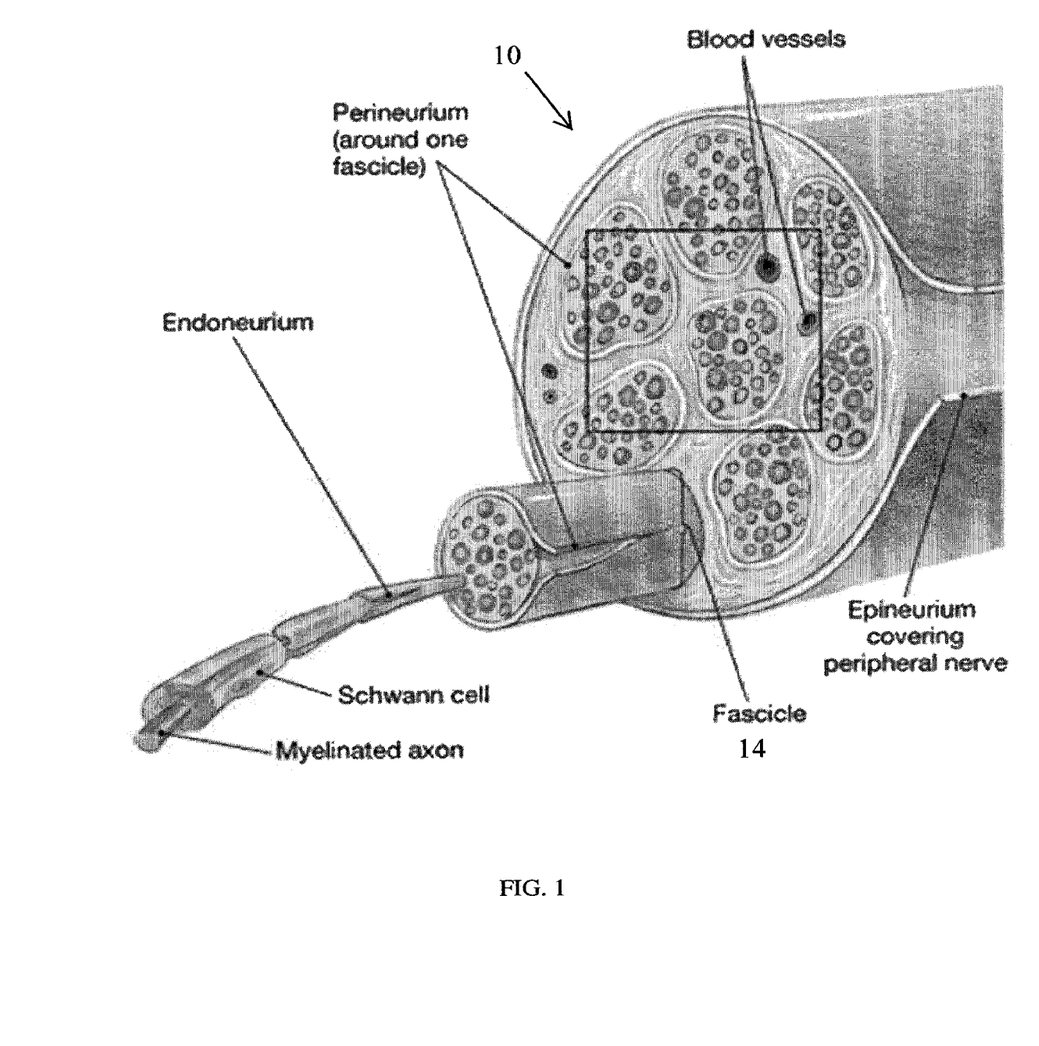
FIG. 1 illustrates the anatomy of a peripheral nerve.

FIG. 1 illustrates the anatomy of a peripheral nerve. As illustrated, a nerve 10 is covered by a layer of tissue called the epineurium. Inside the epineurium, the nerve 10 comprises a plurality of fascicles 14. Each fascicle 14 is covered by a layer of tissue called the perineurium. The fascicle 14 is comprised of a plurality of axons with each axon covered by a layer of tissue called the endoneurium.

Figure 2:
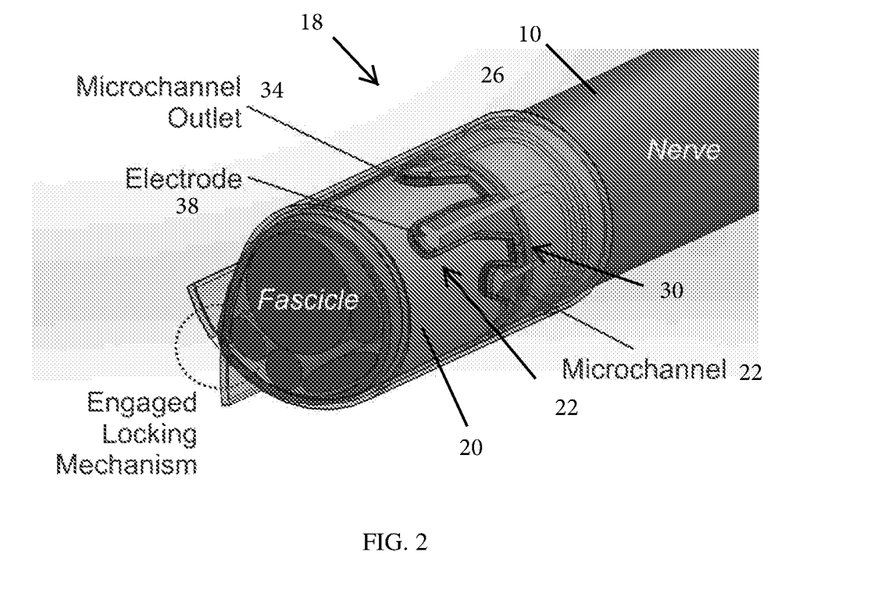
FIG. 2 illustrates a schematic of a cuff electrode positioned on a nerve according to an embodiment of the present invention.

FIG. 2 illustrates a cuff electrode 18 according to an embodiment of the present invention. In particular, FIG. 2 illustrates a Lyse-and-Attract Cuff Electrode. The cuff electrode 18 includes a substrate 20 including an array of microchannels 22 formed therein. Each microchannel 22 includes an inlet 26 in fluid communication with a main supply channel 30. The main supply channel 30 is coupled to a fluid source such as an infusion pump (see FIG. 16). The main supply channel 30 can be shared for sequential or supply of multiple bioactive substances to the microchannels 22. The microchannels 22 carry a fluid such as a lysing agent or a neurotrophic factor that is provided by the fluid source. Each microchannel 22 also includes an outlet 34 in proximity to the nerve 10 to deliver the fluid to the nerve 10 (e.g., an outer surface of the nerve 10). Each microchannel 22 can have a different length and width to vary the time and amount of fluid that exits the outlet 34.

The infusion pump can supply a bioactive substance for activating axonal conductance, such as veratridine, norepinephrine, acetylcholine, adenosine triphosphate, opioid peptides, somatostatin and neuropeptide Y. Additionally, the infusion pump can supply a bioactive substance for blocking axonal conductance, such as capsaicin, pentobarbital, lidocaine, terodotoxin, yohimbine, prazosin, tetraethylammonium, tetrabutyl-ammonium, and 4-aminopyridine.

Figure 7:
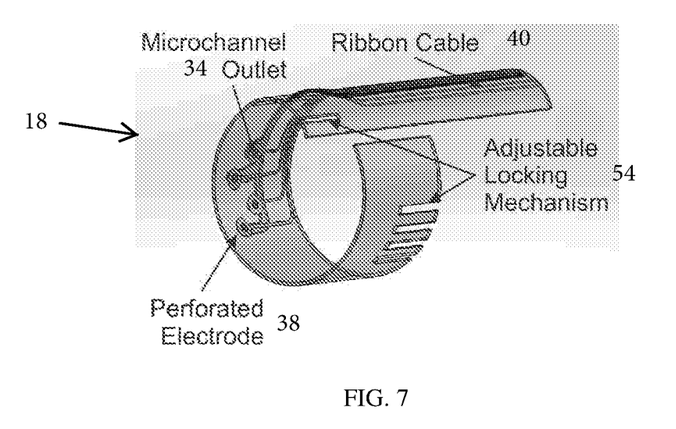
FIG. 7 illustrates a cuff electrode according to an embodiment showing perforated electrodes.
Figure 8:
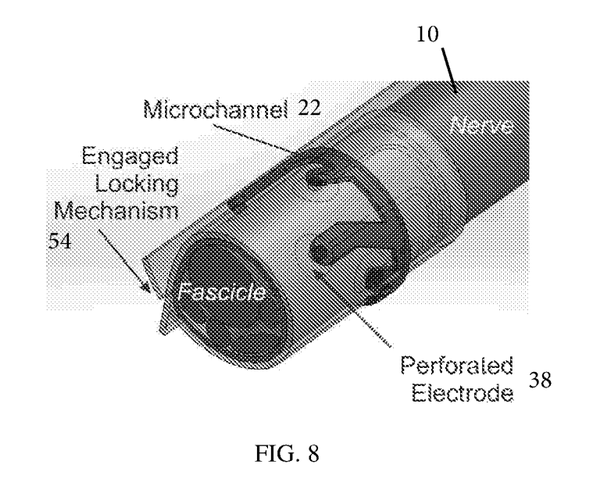
FIG. 8 illustrates the cuff electrode shown in FIG. 7 in a locked orientation.

The cuff electrode 18 also includes an electrode 38 positioned at the outlet 34 of at least one of the microchannels. Each of the electrodes 38 is electrically coupled to a device configured to receive electrical measurements detected by the electrodes 38 or a device configured to stimulate the nerve 10. In other constructions, the cuff electrode 18 can include a plurality of electrodes 38 positioned at the outlet 34, adjacent to the outlet 34, or at a distance from the outlet 34. The electrode 38 can be embedded on an inner surface of the substrate 20 and be positioned in or out of the microchannel 22. The cuff electrode 18 also includes an integrated ribbon cable 40 that routes the electrical connections from each electrode 38 and fluidic connections to custom interconnects (see FIGS. 3 and 16). In still other constructions, the electrodes 38 may be perforated as illustrated in FIGS. 7-8. As an alternative electrode placement, the electrodes 38 can be positioned on an inner surface of the substrate 20 and surround an outlet 34. The electrode is centrally perforated.

Figure 3:
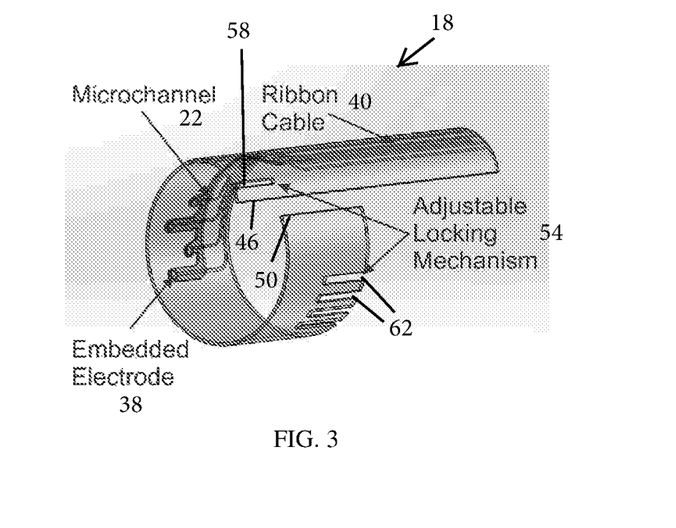
FIG. 3 illustrates the cuff electrode shown in FIG. 2. The image further depicts a cuff electrode after being shaped into a curled format so that it is ready for placement around a nerve.
Figure 4:
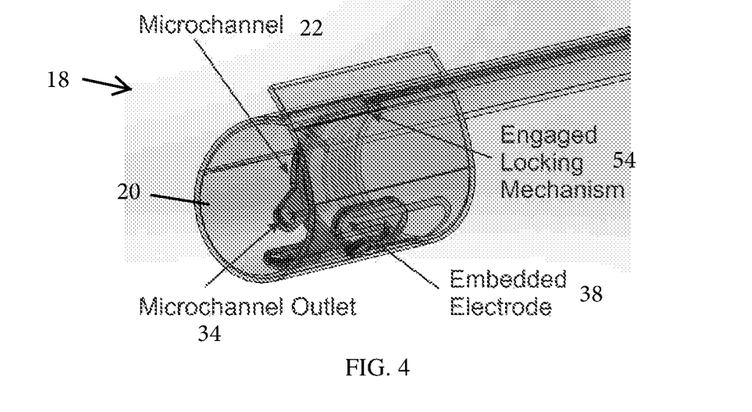
FIG. 4 illustrates the cuff electrode shown in FIG. 2 in a locked orientation.

With reference to FIGS. 3 and 4, the substrate 20 includes a first end 46, a second end 50, and a locking mechanism 54 for coupling the first end 46 and the second end 50. The locking mechanism 54 comprises a first slot 58 formed within the substrate 20 near the first end 46 and a second slot 62 formed within the substrate 20 near the second end 50. The first slot 58 is configured to receive the second slot 62 to thereby couple together the first end 46 and the second end 50. The second end 50 can include a plurality of additional slots similar to second slot 62 such that the cuff electrode can be adjustable and sized and fitted to the outer circumference of the nerve 10. The first slot 58 and the second slot 62 can comprise the same dimensions or be slightly different to accommodate a suitable coupling between the first end 46 and the second end 50.

Figures 9A, 9B:
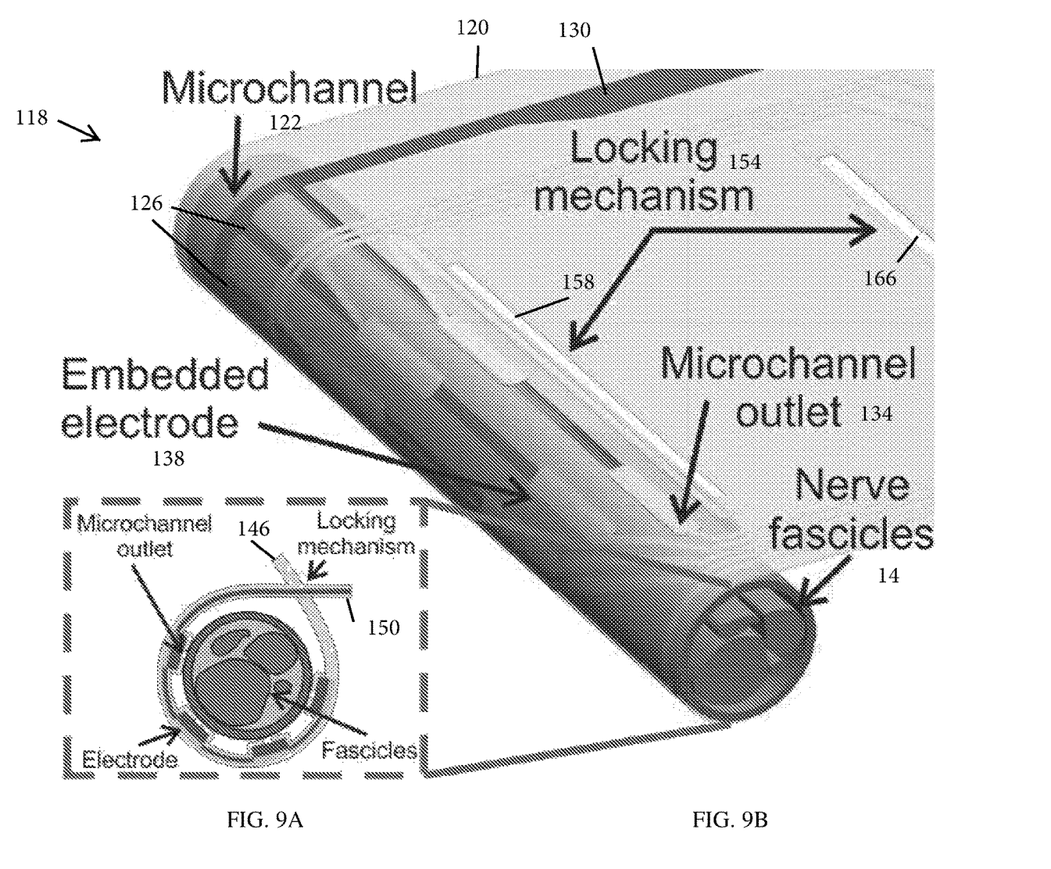
FIG. 9A illustrates a schematic of a cuff electrode according to an embodiment of the present invention.
FIG. 9B is a cross-sectional view of the cuff electrode illustrated in FIG. 9A.

FIGS. 9A and 9B illustrate a cuff electrode 118 according to an embodiment of the present invention. In particular, FIGS. 9A and 9B illustrate a Lyse-and-Attract Cuff Electrode. The cuff electrode 118 includes a substrate 120 including an array of microchannels 122 formed therein. Each microchannel 122 includes an inlet 126 in fluid communication with a main supply channel 130. The main supply channel 130 is coupled to a fluid source such as an infusion pump (see FIG. 16). The main supply channel 130 can be shared for sequential or supply of multiple bioactive substances to the microchannels 22. The microchannels 122 carry a fluid such as a lysing agent or a neurotrophic factor that is provided by the fluid source. Each microchannel 122 also includes an outlet 134 in proximity to the nerve 10 to deliver the fluid to the nerve 10 (e.g., an outer surface of the nerve 10). Each microchannel 122 can have a different length and width to vary the time and amount of fluid that exits the outlet 134.

Like the embodiment describing the cuff electrode 18, the infusion pump can supply a bioactive substance for activating axonal conductance, such as veratridine, norepinephrine, acetylcholine, adenosine triphosphate, opioid peptides, somatostatin and neuropeptide Y. Additionally, the infusion pump can supply a bioactive substance for blocking axonal conductance, such as capsaicin, pentobarbital, lidocaine, terodotoxin, yohimbine, prazosin, tetraethylammonium, tetrabutyl-ammonium, and 4-aminopyridine.

The cuff electrode 118 also includes an electrode 138 positioned at the outlet 134 of at least one of the microchannels. As illustrated in FIG. 9B, each microchannel 122 includes a plurality (e.g., two) of electrodes 138. Each of the electrodes 138 is electrically coupled to a device configured to receive electrical measurements detected by the electrodes 138 or a device configured to stimulate the nerve 10. In other constructions, the cuff electrode 118 can include a plurality of electrodes 138 positioned at the outlet 134, adjacent to the outlet 134, or at a distance from the outlet 134. The electrode 138 can be embedded on an inner surface of the substrate 20 and be positioned in or out of the microchannel 122. The cuff electrode 118 also includes an integrated ribbon cable 140 that routes the electrical connections from each electrode 138 and fluidic connections to custom interconnects (see FIGS. 10 and 16). In still other constructions, the electrodes 138 may be perforated as illustrated in FIGS. 7-8. As an alternative electrode placement, the electrodes 138 can be positioned on an inner surface of the substrate 120 and surround an outlet 134. The electrode is centrally perforated.

Figure 10:
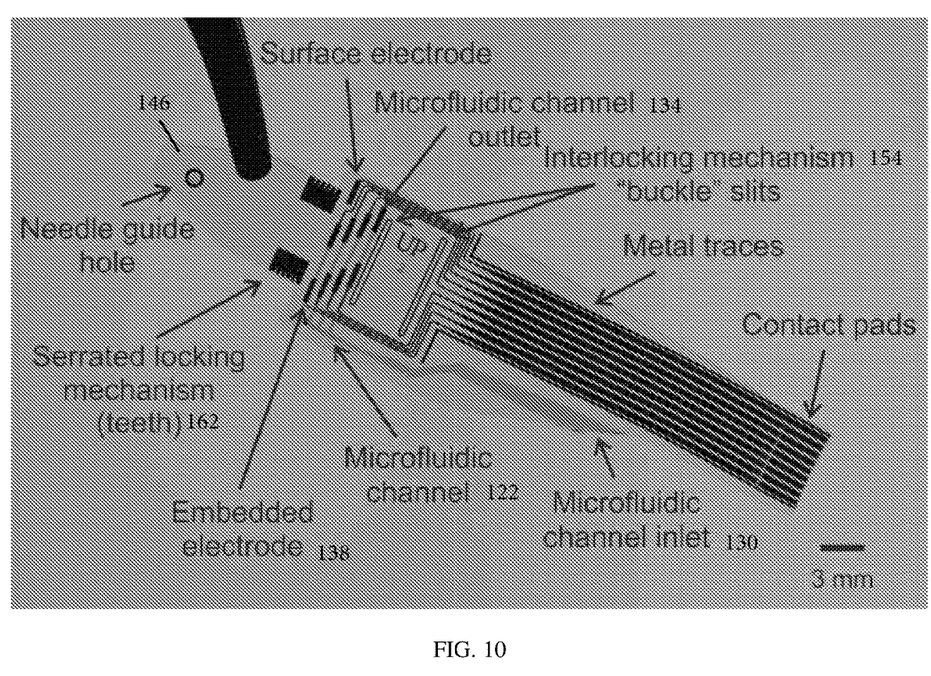
FIG. 10 illustrates a fabricated cuff electrode.

As illustrated in FIGS. 9A, 9B, and 10, the substrate 120 includes a first end 146, a second end 150, and a locking mechanism 154. The locking mechanism 154 comprises a first slot 158 formed within the substrate 120 and serrated teeth 162. The first slot 158 is configured to receive the first end 146 and the serrated teeth 162 to form a tube around the nerve 10. The substrate 120 includes a perimeter defined by a plurality of edges. The edge at the first end 146 can have a width less than a width of the substrate 120 in the area of the first slot 158. The first slot 158 thereby includes a length configured or is dimensioned to receive the edge at the first end 146 and the serrated teeth 162. A second slot 166 is configured to receive the first end 146 after it has passed through first slot 158. The second slot 166 is an additional feature intended to better retain the first end 146 and prevent it from slipping out during use.

Figure 5:
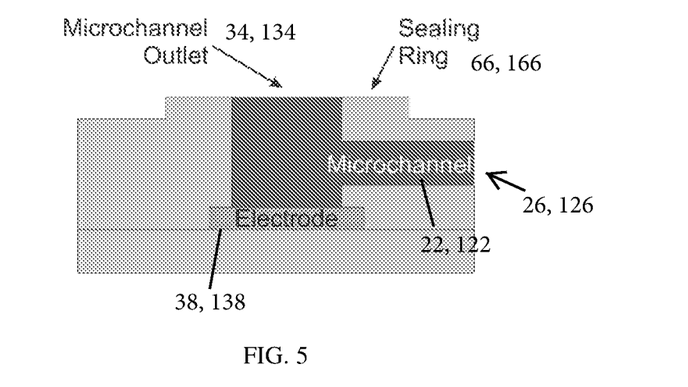
FIG. 5 is a cross-sectional view of a portion of the cuff electrode shown in FIG. 2 and further illustrating a sealing ring.
Figure 6:
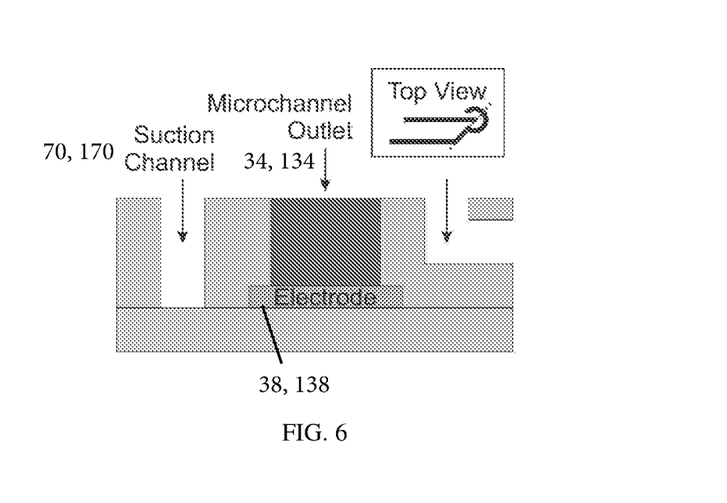
FIG. 6 is a cross-sectional view of a portion of the cuff electrode shown in FIG. 2 and further illustrating a suction channel. The inset shows the layout of the two channels; the dotted red line shows where the cross section was taken, bisecting the delivery microchannel.

The cuff electrode 18, 118 can include a sealing ring 66, 166 positioned at the outlet 34, 134 of the microchannel 22, 122 as illustrated in FIGS. 5 and 6. The sealing ring 66, 166 can provide a seal (or partial seal) with the nerve 10 and prevent significant leakage of the fluid beyond the target location on the nerve 10. The cuff electrode 18, 118 can also include a suction channel 70, 170 in communication with a vacuum source to suction excess fluid at the outlet 34, 134. For example, a gentle suction may be applied to the same microchannel immediately after infusion (see FIG. 5) or the inclusion of a separate ring-shaped microchannel to surround the infusion outlet (see FIG. 6) and provide suction to the nerve 10 in order to limit lateral leakage of the infused fluid. The drawback of the latter approach is the increase in complexity of the fabrication and therefore time required to complete one fabrication run of the cuff electrode.

If the signal-to-noise ratio or fascicular selectivity are insufficiently improved for the placement of electrodes 38, 138 inside the microchannel 22, 122, the electrodes may be alternatively placed on an inner surface of the substrate 20, 120 as depicted in FIGS. 7 and 8.

FIG. 10 illustrates a fabricated cuff electrode 118. The cuff electrode 118 is dimensioned to fit around a nerve 10 that has a diameter of about 1 mm to about 1.5 mm. The cuff electrode 118 is about 1.5 mm by about 0.3 mm.

Figure 11:
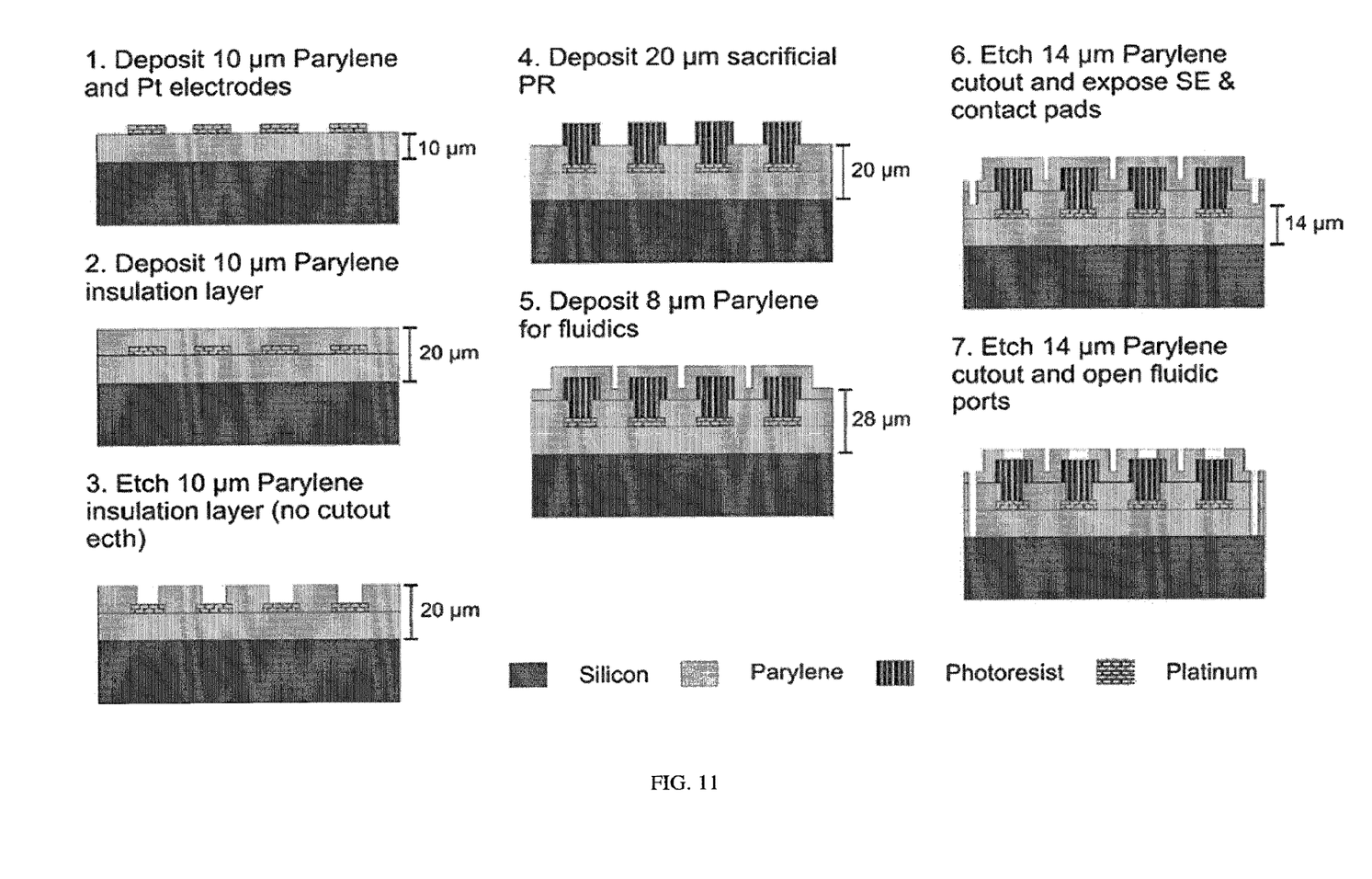
FIG. 11 illustrates a method of fabricating a cuff electrode according to an embodiment of the present invention.

FIG. 11 illustrates a method of fabricating the cuff electrodes 18, 118 according to an embodiment of the present invention. The cuff electrode 18, 118 can be fabricated in batches using Parylene C surface micromachining technology. Immediately after microfabrication, the cuff electrode is flat. The thin film Parylene substrate is flexible to allow wrapping around a nerve. In one construction, the cuff electrode 18, 118 can have a total thickness of at least 20 µm to facilitate handling and improve barrier properties. During fabrication, the Parylene film is supported by a Si carrier wafer with a native oxide layer which facilitates release of the cuff electrode at the end of the fabrication process. (See step 1) Each Parylene layer is approximately 10 µm thick. The thin film metal traces are Pt (2000 Å). Pt features are formed using a thin film metal lift-off process and the metal is deposited using e-beam evaporation. Metal traces are insulated in Parylene and then electrode sites are opened in oxygen plasma. (See steps 2 and 3) Microchannels are then formed using sacrificial photoresist followed by a final Parylene layer capping the microchannel. (See steps 4 and 5) An oxygen plasma step opens contact pad sites as well as etch the outline defining each electrode. (See steps 6 and 7) At the conclusion of the fabrication process, individual LACE is released in a water bath and then the microchannels released in successive immersions in acetone, isopropyl alcohol, and DI water. If necessary, the microchannel inlets on the ribbon cable may be covered in a thick film layer of photosensitive SU-8 epoxy to prevent their collapse during handling.

Optionally, the cuff electrode 18, 118 may be thermoformed. In this process, the cuff electrode 18, 118 is wrapped around a small diameter rod and heated above the Parylene glass transition temperature in a vacuum oven. This allows the thermoplastic Parylene to take on the shape of the rod after the film is cooled and the rod removed. The purpose of this step is to pre-curve the cuff to a small diameter mold and thereby facilitate surgical application to the nerve 10.

Example

Figure 12:
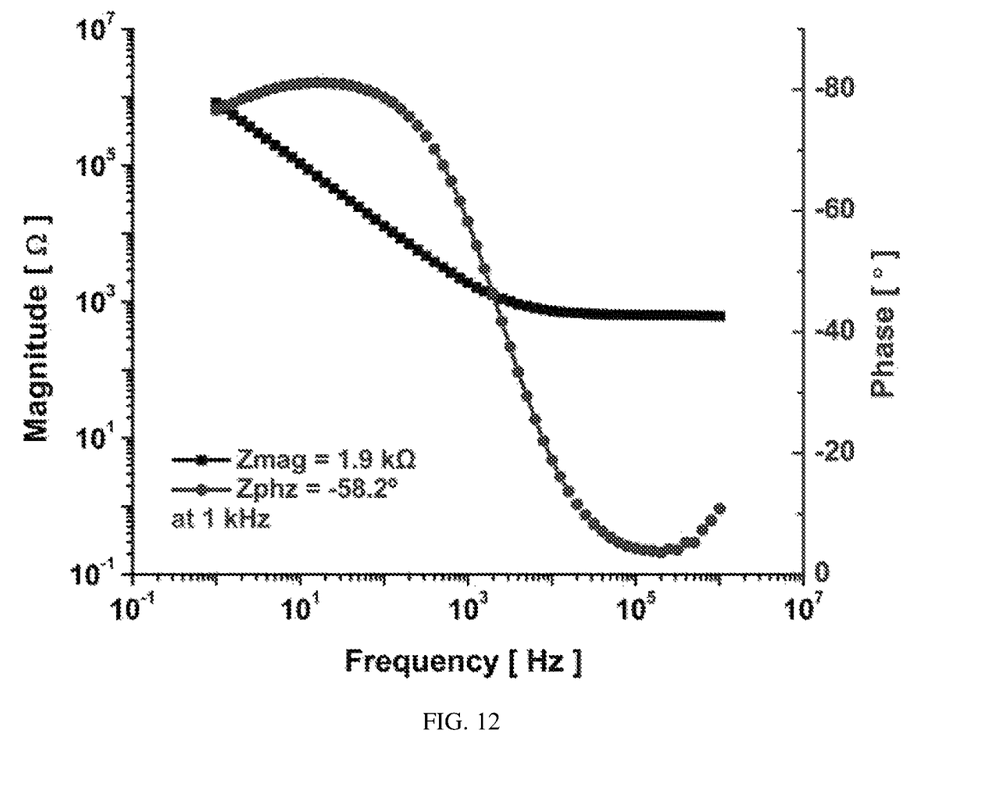
FIG. 12 graphically illustrates electrochemical impedance spectroscopy plots of impedance magnitude and phase for a surface electrode after CV clean.
Figure 13:
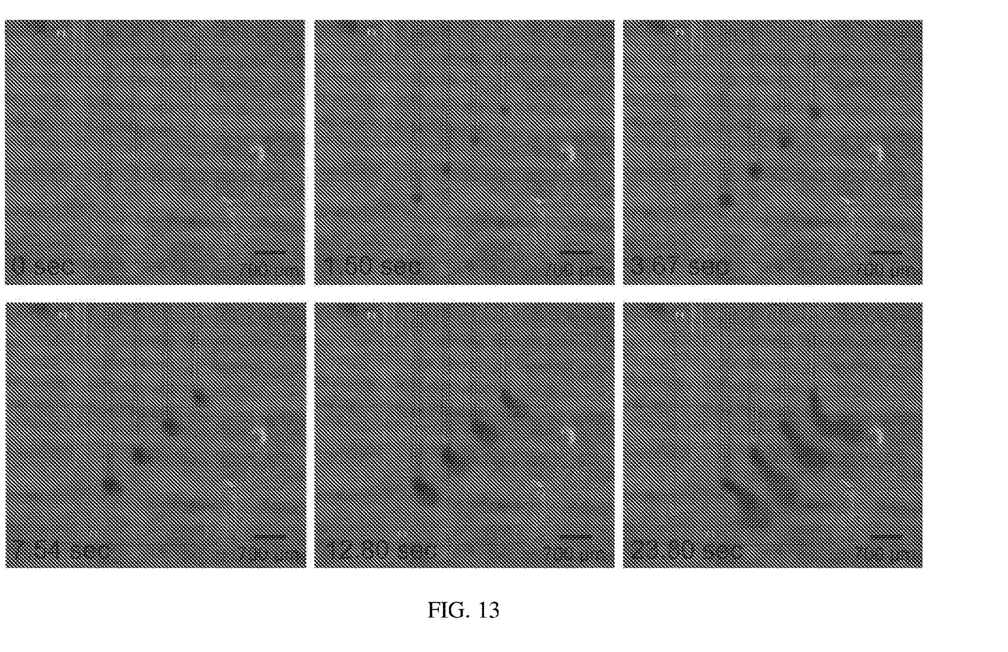
FIG. 13 illustrates sequential photographs of an infusion experiment at 0.83 µL/min flow rate. The channels were primed with ink introduced at the microfluidic inlet channel.
Figure 14:
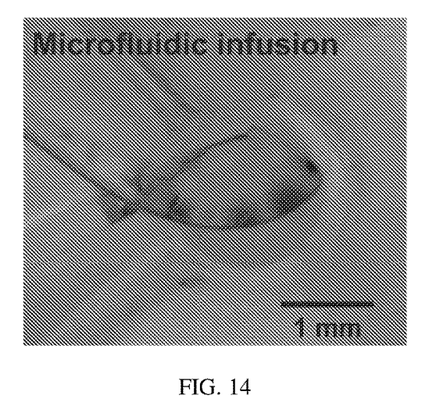
FIG. 14 illustrates infusion of a curled cuff.
Figure 15:
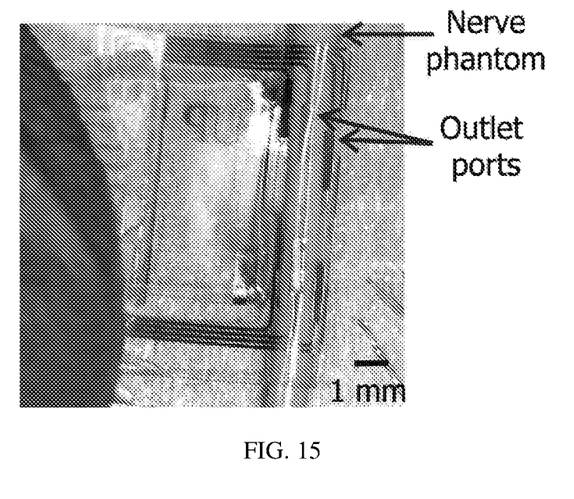
FIG. 15 illustrates a cuff electrode wrapped around a nerve phantom.
Figure 16:
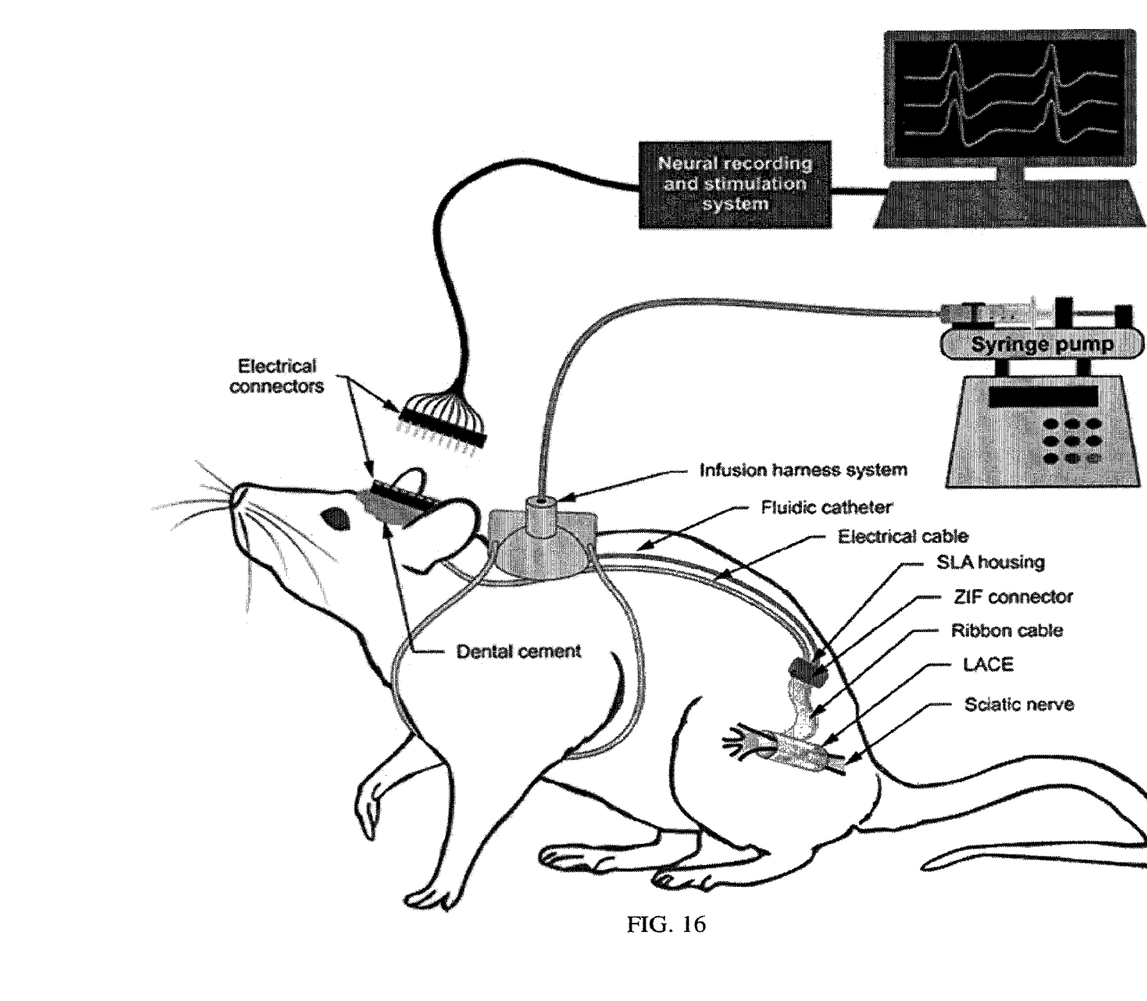
FIG. 16 illustrates an example of an application of a cuff electrode according to an embodiment of the invention.

An electrode cuff 118 as illustrated in FIG. 10 was fabricated. The electrochemical impedance of the surface electrode 140 were measured and plotted as illustrated in FIG. 12. The surface electrode 140 bears the same dimensions as the embedded electrode 138 in the embodiment shown in FIG. 10. In addition, the array of microchannels 122 was primed with ink. The main supply channel 130 of the electrode cuff 118 was then coupled to a fluid source. The fluid was delivered at 0.83 µL/min flow rate through the main supply channel 130 and to the array of microchannels 122. FIGS. 13 and 14 show sequential photographs of the fluid traveling through the array of microchannels 122 and exiting the outlets 134 at the same time and amount in this embodiment. The microchannel lengths may be designed to alter the time fluid exits and the relative amount between microchannels on the cuff. FIG. 14 further shows the fluid exiting the outlets 134 in the array of microchannels 122 in a curled cuff electrode 118. FIG. 15 illustrates the electrode cuff 118 wrapped around a nerve phantom with the locking mechanism fully engaged. FIG. 16 illustrates an electrode cuff showing the ribbon cable containing the electrode traces and supply microchannel with additional connections required to operate the device in a live animal.

Figure 17:
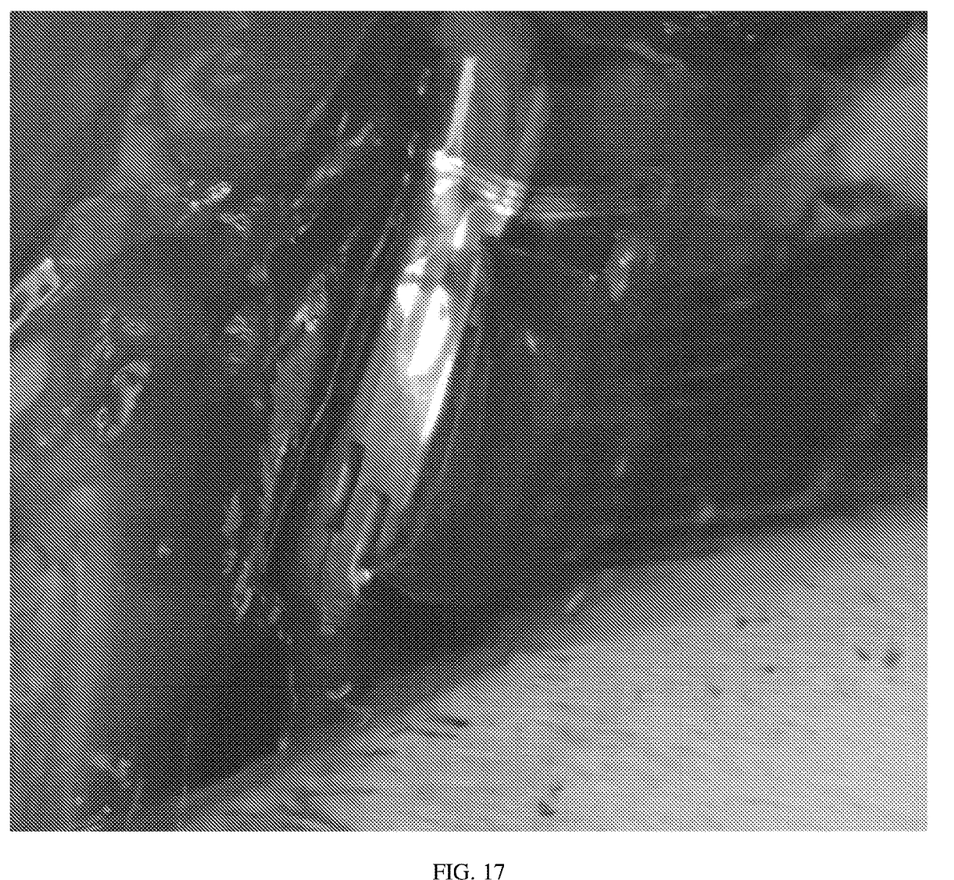
FIG. 17 illustrates a cuff electrode applied to a sciatic nerve of a rat.

FIG. 17 illustrates a cuff electrode 118 applied to a sciatic nerve of a rat.

The present disclosure described herein and representative embodiments, are exemplary, and are not intended as limitations on the scope of the invention. Changes therein and other uses will occur to those skilled in the art which are encompassed within the spirit of the invention as defined by the scope of the claims.

What is claimed is:
1. A cuff electrode comprising:
a flexible polymer substrate including an array of elongated microchannels for fluid delivery formed along a surface of the substrate, at least one of the microchannels includes an inlet and an outlet, the flexible polymer substrate configured to be applied around a nerve;
an electrode positioned adjacent to the outlet of the at least one microchannel; and
a supply channel in fluid communication with the at least one microchannel, the supply channel providing a lysing agent or a neurotrophic factor to the outlet of the at least one microchannel for delivery of the lysing agent or the neurotrophic factor to an exterior surface of the nerve.

2. The cuff electrode of claim 1, wherein the electrode is configured to measure or stimulate electrical activity of an axon of a nerve.

3. The cuff electrode of claim 1, wherein the flexible polymer substrate is partially comprised of Parylene.

4. The cuff electrode of claim 1, wherein the electrode is partially comprised of Platinum.

5. The cuff electrode of claim 1, further comprising a sealing ring positioned at the outlet to at least partially seal to a biological tissue.

6. The cuff electrode of claim 1, further comprising a suction channel formed at least around the outlet for suctioning excess fluid at the outlet.

7. The cuff electrode of claim 1, wherein the electrode is positioned on an inner surface of the substrate.

8. The cuff electrode of claim 7, wherein the electrode is centrally perforated and is positioned at an outer circumference of the outlet.

9. The cuff electrode of claim 1, further comprising an adjustable locking mechanism.

10. The cuff electrode of claim 9, wherein the adjustable locking mechanism comprises a set of serrated teeth configured to interlock with a slot.

11. The cuff electrode of claim 9, wherein the adjustable locking mechanism comprises a first slot configured to interlock with a second slot.

12. The cuff electrode of claim 1, wherein the main supply channel is coupleable to an infusion pump to provide the lysing agent to the array of microchannels.

13. The cuff electrode of claim 1, wherein each of the microchannels in the array of microchannels includes a length and a width, and wherein the length and width are variable to alter the time when fluid exits the respective outlets and the relative output volume of fluid that exits the respective outlets.

14. A cuff electrode comprising:
a substrate including an array of elongated microchannels for fluid delivery along a surface of the substrate, each of the microchannels having an inlet connected to a main supply channel, and an outlet positioned adjacent to an exterior surface of a nerve, the outlet configured to deliver the fluid to the exterior surface of the nerve;
an electrode positioned in the microchannel for detecting or stimulating electrical activity of the nerve;
an adjustable locking mechanism configured to position the substrate around a nerve having a diameter between about 1 mm and about 2 mm,
wherein the fluid is a lysing agent or a neurotrophic factor.

15. The cuff electrode of claim 14, wherein the main supply channel is coupleable to an infusion pump for supplying the lysing agent to the array of microchannels.

16. The cuff electrode of claim 15, wherein the lysing agent is collagenase elastase, gelatinase, galactosidase, lactamase, glucuronidase, tripsin, fibrinolysin, papain, or other enzyme involved in digestion of the collagen-mucopolysaccharide-containing extracellular matrix.

17. The cuff electrode of claim 14, wherein the main supply channel is coupleable to an infusion pump for supplying the neurotrophic factor.

18. The cuff electrode of claim 17, wherein the neurotrophic factor is a neurotrophin, such as NGF, BDNF, NT-3, or NT-4.

19. The cuff electrode of claim 17, wherein the neurotrophic factor is methylcobalamin.

20. The cuff electrode of claim 14, wherein the main supply channel is coupleable to an infusion pump for supplying a bioactive substance for activating axonal conductance, such as veratridine, norepinephrine, acetylcholine, adenosine triphosphate, opioid peptides, somatostatin and neuropeptide Y.

21. The cuff electrode of claim 14, wherein the main supply channel is coupleable to an infusion pump for supplying a bioactive substance for blocking axonal conductance, such as capsaicin, pentobarbital, lidocaine, terodotoxin, yohimbine, prazosin, tetraethylammonium, tetrabutyl-ammonium, and 4-aminopyridine.

22. The cuff electrode of claim 14, wherein the main supply channel can be shared for sequential or supply of multiple bioactive substances to the microchannels.

23. The cuff electrode of claim 14, wherein the adjustable locking mechanism comprises a first slot shaped to interlock with a second slot.

24. The cuff electrode of claim 14, wherein the adjustable locking mechanism comprises a set of serrated teeth and at least one slot to receive at least one of the plurality of serrated teeth.

25. The cuff electrode of claim 14, wherein the electrode is centrally perforated and is positioned at an outer circumference of the outlet.

26. The cuff electrode of claim 14, wherein each of the microchannels in the array of microchannels includes a length and a width, and wherein the length and width are variable to alter the time when fluid exits the respective outlets and the relative output volume of fluid that exits the respective outlets.

27. The cuff electrode of claim 14, wherein the substrate includes an interior surface, and wherein the electrode is positioned on the interior surface.

* * * * *